(12) United States Patent  (10) Patent No.: US 6,649,236 B2
Haskin                          (45) Date of Patent:       Nov. 18, 2003

(54) ANTI-FOMITIC DEVICES

(76) Inventor: Marvin E. Haskin, 400 Bryn Mawr Ave., Bryn Mawr, PA (US) 19010-2101

(*) Notice: Subject to any disclaimer, the term of this patent is extended or adjusted under 35 U.S.C. 154(b) by 0 days.

(21) Appl. No.: 10/277,304

(22) Filed: Oct. 22, 2002

(65) Prior Publication Data

US 2003/0077408 A1 Apr. 24, 2003

Related U.S. Application Data

(63) Continuation of application No. 08/923,866, filed on Sep. 4, 1997, now Pat. No. 6,468,611.

(51) Int. Cl.[7] .................. A61B 19/02; B65D 75/30; B65D 85/00
(52) U.S. Cl. .................. 428/35.2; 206/41.7; 206/200; 206/438; 206/455; 383/42; 383/63; 383/64; 383/93; 383/95; 383/97; 383/98; 383/211; 428/35.4; 428/35.7; 428/121; 428/124
(58) Field of Search .................. 428/35.2, 354, 428/35.7, 121, 124; 206/41.7, 200, 438, 455; 383/42, 63, 64, 93, 95, 97, 98, 211

(56) References Cited

U.S. PATENT DOCUMENTS

| 2,161,058 A | 6/1939 | Kamiss | 250/68 |
|---|---|---|---|
| 3,092,252 A | 6/1963 | Brause et al. | 206/63.2 |
| 3,215,265 A | 11/1965 | Welin-Berger | 206/63.2 |
| 3,843,041 A | 10/1974 | Oliverius | 229/62 |
| 3,847,280 A | 11/1974 | Poncy | 206/306 |
| 3,941,245 A | 3/1976 | Oliverius | 206/438 |
| 3,988,873 A | 11/1976 | Oliverius | 53/27 |
| 4,057,731 A | 11/1977 | Loseff | 250/475 |
| 4,275,812 A | 6/1981 | Poncy et al. | 206/278 |
| 4,348,440 A | 9/1982 | Kriozere | 428/41 |
| 4,410,130 A | 10/1983 | Herrington | 383/62 |
| 4,445,241 A | 5/1984 | Ender et al. | 5/468 |

(List continued on next page.)

OTHER PUBLICATIONS

Haskin et al., "The Possible Role of Hospital Radiology Departments in Cross Infection and Antibiotic–resistant Bacterail Mutagenesis," *Surgical Clinics of North America* vol. 50 (4) pp. 945–952 (1970).

*Primary Examiner*—Sandra M. Nolan
(74) *Attorney, Agent, or Firm*—Roberts Abokhair & Mardula, LLC

(57) ABSTRACT

An anti-fomitic device in the form of a bag or envelope forms a cover for an object for preventing cross-infection by bacteria and other pathogens that may reside on the object. The anti-fomitic device is a flat, flexible bag or envelope with a closure means at one or both ends of the bag or envelope, having a sterile interior that is sealed during manufacture to maintain sterility. Therefore, no outer wrapping for the anti-fomitic device is required. The anti-fomitic device is inverted when used to cover the object and results in an ultimate outer surface that is initially sterile. Materials for the coverings/bags are impervious to the transmission of pathogens. A laundered covering such as a sheet, pillowcase, etc., can then be slipped over the object that is covered with the anti-fomitic device to enhance comfort, yet maintain protection against pathogens on the object being covered.

14 Claims, 4 Drawing Sheets

U.S. PATENT DOCUMENTS

| | | | |
|---|---|---|---|
| 4,525,409 A | 6/1985 | Elesh | 428/193 |
| 4,553,538 A | 11/1985 | Rafelson | 128/132 |
| 4,770,911 A | 9/1988 | Sengewald | 428/35 |
| 4,832,009 A | 5/1989 | Dillon | 128/156 |
| 4,902,543 A | 2/1990 | Ernst | 428/35.2 |
| 4,923,453 A | 5/1990 | Bullard, Jr. | 604/356 |
| 5,050,256 A | 9/1991 | Woodcock | 5/448 |
| 5,123,535 A | 6/1992 | Patnode et al. | 206/438 |
| 5,162,040 A | 11/1992 | Annett | 602/57 |
| 5,178,278 A | 1/1993 | Oliverius | 206/455 |
| 5,227,218 A | 7/1993 | Herum | 428/128 |
| 5,228,851 A | 7/1993 | Burton | 433/116 |
| 5,343,861 A | 9/1994 | Herman | 128/652 |
| 5,365,023 A | 11/1994 | Lawton | 181/131 |
| 5,466,897 A | 11/1995 | Ross et al. | 181/131 |
| 5,541,972 A | 7/1996 | Anthony | 378/37 |
| 5,554,098 A | 9/1996 | Yabe et al. | 600/121 |
| 5,564,431 A | 10/1996 | Seward | 128/715 |
| 5,566,410 A | 10/1996 | Schaechter | 5/490 |
| 5,599,093 A | 2/1997 | Hoftman et al. | 362/400 |
| 5,643,189 A | 7/1997 | Masini | 602/58 |
| 5,711,841 A | 1/1998 | Jaker | 156/308.4 |
| 6,468,611 B1 * | 10/2002 | Haskin | 428/35.2 |

* cited by examiner

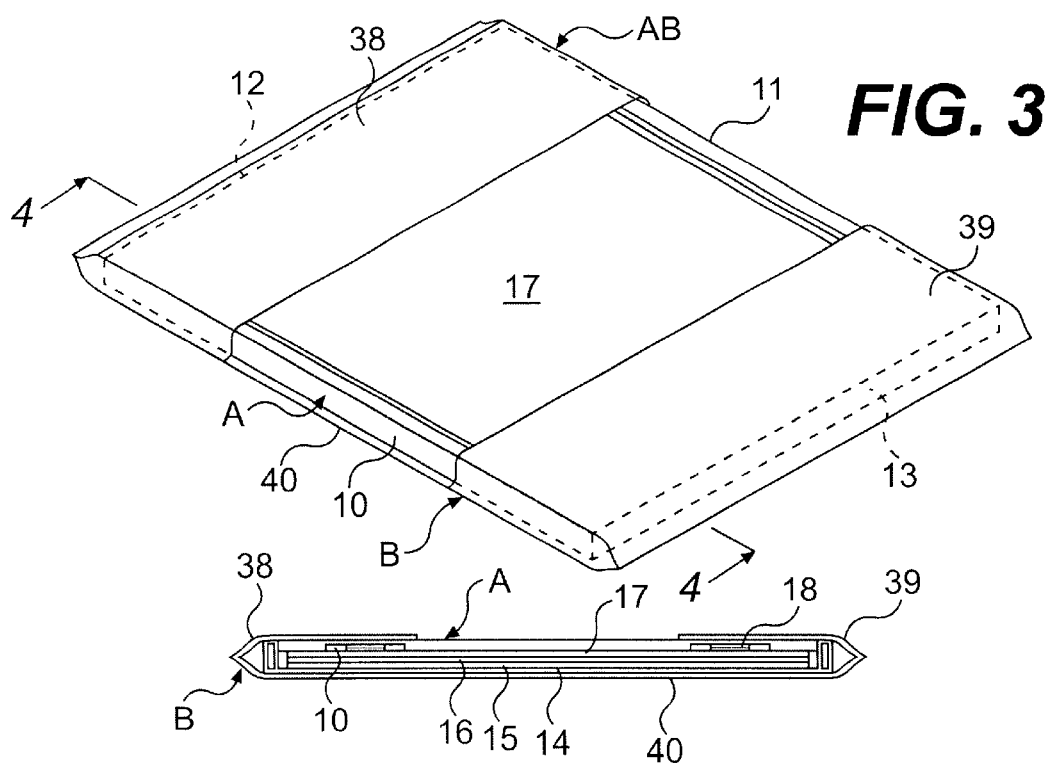
FIG. 3
FIG. 4
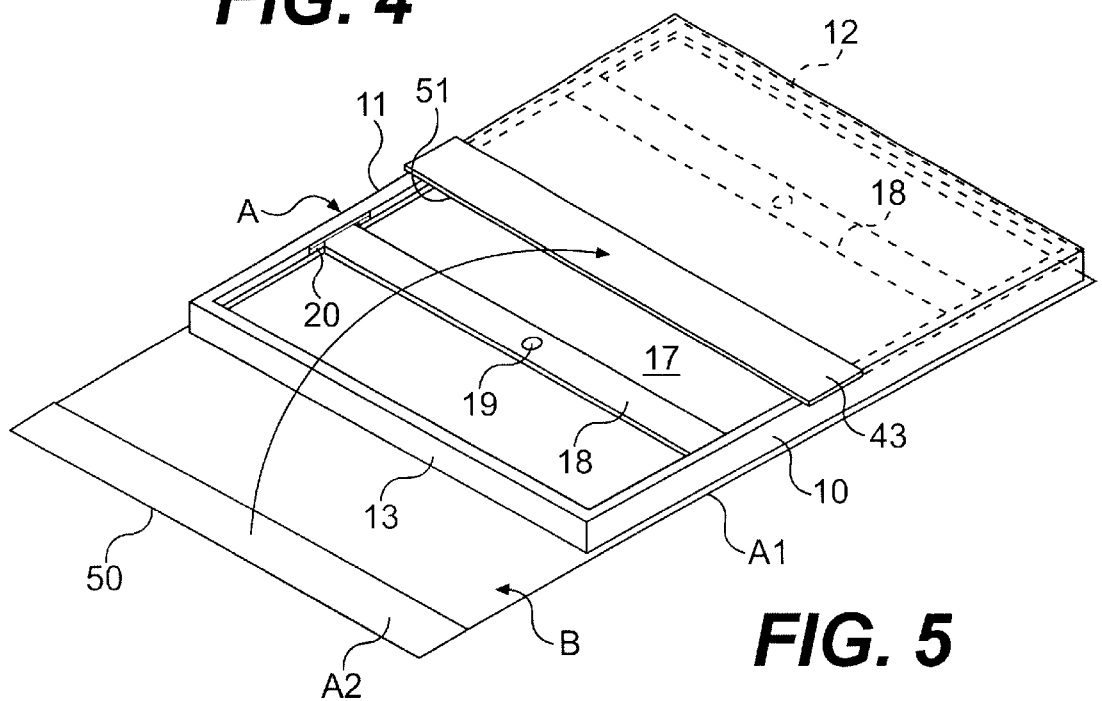
FIG. 5

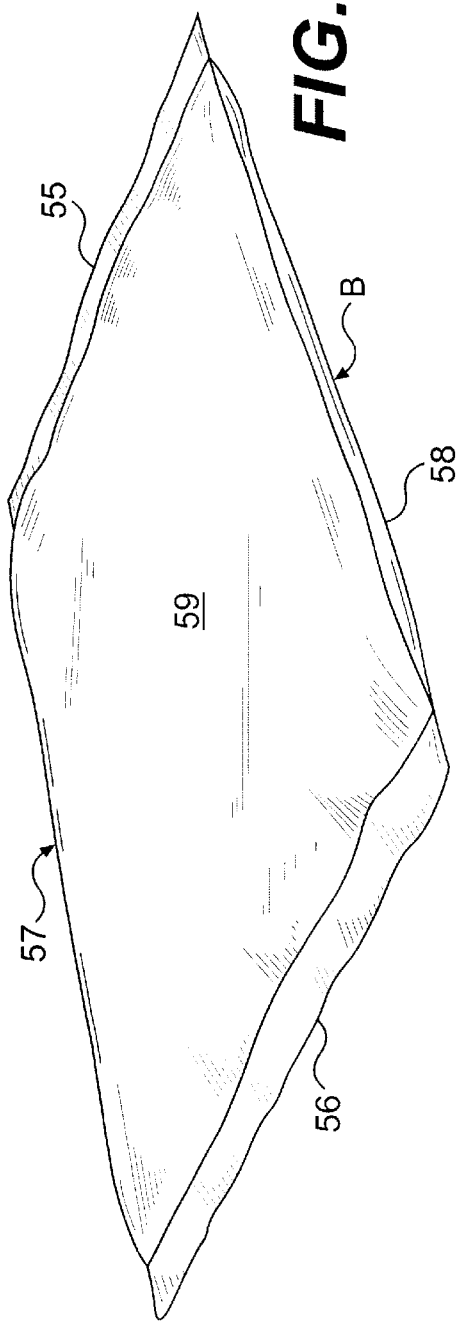
FIG. 8
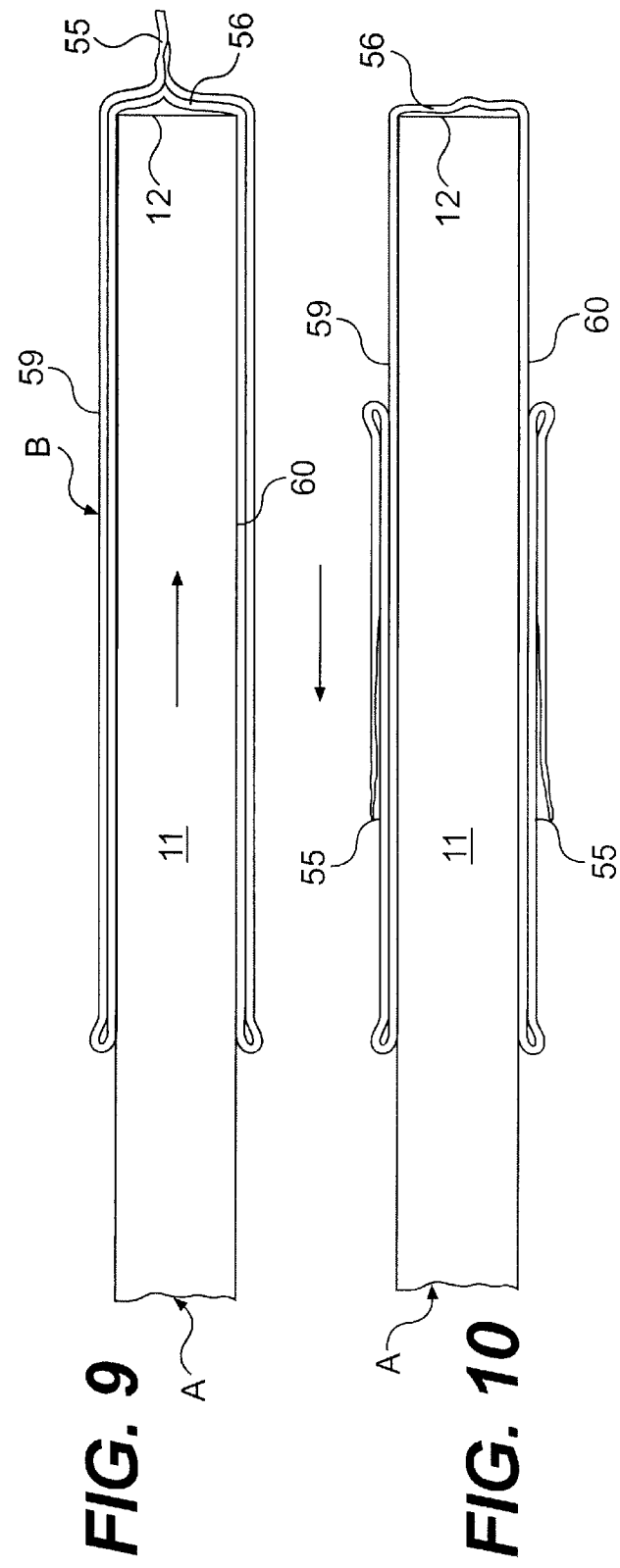
FIG. 9
FIG. 10

ANTI-FOMITIC DEVICES

RELATIONSHIP TO OTHER APPLICATIONS

This application is a continuation of U.S. application Ser. No.: 08/923,866, filed Sep. 4, 1997, issued as U.S. Pat. No. 6,468,611 on Oct. 22, 2002, which is hereby incorporated by reference.

FIELD OF THE INVENTION

The present invention relates generally to a cover or barrier to prevent cross-infection. In particular, the present invention relates to a range of anti-fomitic covers to prevent cross-infection, including such covers for pillows, mattresses, X-ray cassettes, surgical and diagnostic equipment, toilet seats, table and chair seat surfaces, wash basin faucet handles and other handles, etc., as well as covers such as diapers or other similar sorts of "clothing," for example, surgical robes, shoe covers for the surgical room, etc.

BACKGROUND OF THE INVENTION

The problems of cross-infection and the production of antibiotic-resistant mutations have been subjects for concern in hospital settings, as well as in household and other settings, such as the hopitality industry (hotels, motels, bed and breakfast businesses, hostels, etc.). These problems are particularly problematic for those with compromised immune systems or with special bacterial, viral fungal, parasitic, or other susceptibilities. The latter category of special susceptibilities may also include persons with allergies, and persons who develop one or more of a range of contact dermatitises, to name but a few non-limiting examples.

One means of transmitting bacteria, viruses, fungi, and other pathogens is by fomites, which are inanimate agents of such transmissions, including, for example, bedding, toilet seats, clothes, table tops and other fixed surfaces, surgical and X-ray equipment, etc. Thus, a fomite (also called a fomes) may absorb or otherwise harbor one or more strains of pathogenic bacteria, fungi, viruses, etc., and later transmit those pathogens, by contact, to a human.

A common fomite found in hospitals is metallic X-ray cassettes. Both patients and hospital staff may handle or otherwise touch an X-ray cassette, depending on the X-ray system used and the particular application. For example, in some applications, an undraped patient may hold an X-ray cassette in position against a portion of his body during X-ray filming. Subsequent to the filming, one or more hospital staff members may also touch the X-ray cassette during the progression culminating in photographic development of the X-ray film.

Another common fomite is bedding, where commonly employed materials, such as cotton, act as wicks to carry pathogens far from the initial contact point with human skin, particularly when moisture is present (sweat, semen, saliva, vaginal secretions, secretions from wounds and open pimples, spilled drinks, etc.). Thus, when sheets and pillow cases are changed, the deeper lying material (mattress, mattress cover, pillow) still harbors potential pathogens of the previous user(s). Furthermore, the next user— particularly when moisture is introduced onto the "scene"— can become infected by reverse wicking; i.e., moisture can draw deep lying pathogens back toward the surface of the bedding that is in contact with the user.

Similar to bedding, clothing and related items (such as diapers, surgical robes and covers) also are subject to the problem of passing pathogens from the person wearing the item to another person or surface into which the item comes into contact. Again, as with bedding, the problem of cross-contamination is exacerbated by wicking in the presence of moisture.

Another common fomite is the surfaces encountered in bathrooms As has been well documented for decades, toilet seats, the faucet handles of wash basins, door handles, etc., and other surfaces in bathrooms are commonly contaminated with *E. coli* and other pathogens. As but one illustration of the problem, one need only recognize that a user of a toilet often will leave the toilet with substantial *E. coli* contamination of at least one hand. That individual may then, in turn, contaminate the knob/handle of the toilet stall, and then one or more faucet handles at a wash basin. Said individual then washes his hands, but touches the one or more faucet handles that he had just contaminated in the process of turning off the water flow, thereby re-contaminating his hand(s). Thus, whatever is subsequently touched by the *E. coli*-contaminated hand(s) of that individual will also become so contaminated.

As another example of cross-contamination in the bathroom setting, pathogens on toilet seats may be tranmittable to the next user. One such example is the herpes viruses, which may be transmitted to a subsequent contactor, particularly if that individual has an open wound. Other pathogens may similarly be so transmitted, though some will require relatively immediate contact by the next person when the pathogen is not hardy outside a "biological" setting (i.e., a setting having the requisite moisture and/or temperature close to human interior body temperature).

Yet another setting that is ripe for cross-contamination is the kitchen. Not only is there the well documented potential problems with contamination sources such as chicken skin (Salmonella, etc.), raw beef (*E. coli*, etc.), and insects and other bugs and parts thereof (keeping in mind that the FDA allows such contamination to prescribed levels), but also *E. coli* contamination due to the use of toilets by the kitchen worker (or from contamination by a previous user of the toilet). In the same manner noted above in the context of bathrooms, cross-contamination of faucet handles of wash basins/sinks in kitchens is wide spread. The kitchen cross-contamination problem may also be extended to include problems from the use of cutting boards (problematic particularly with porous material like wood) and from inadequate cooking of contaminated food. In addition, inadequate cleaning of virtually all kitchen surfaces into which human skin comes into contact, directly or indirectly, further compounds the problem of cross-contamination; and this would include not only faucet handles, but also table, counter and other surfaces, as well as handles to ovens, refrigerators, microwave units, etc.

One study of hospitals (*Surgical Clinics of North America* 50 [No. 4]: pages 945–952, August 1970) included analysis of portions of X-ray rooms and X-ray equipment, including cassettes used in portable X-ray machines. Organisms cultured from these cassettes included *staphylococcus aureus* (coagulase negative), *staphylococcus aureus* (coagulase positive), *streptococcus viridans*, aspergillus, fungus, and diptheroids. The cassettes cultured in this study included ones placed in direct contact with undraped patients.

U.S. Pat. No. 3,092,252 to Brause. et al. discloses packages with folds at one end for use in protecting humans from pathogens that otherwise might be present on thermometers, tongue depressors, surgical instruments, fingers/hands, etc. The inner surface of the packages of this invention initially are sterile, though the objects placed within the packaging are not sterile. Multiple folds are utilized in the practice of this invention. Complicated folding is utilized in the packaging of this invention.

U.S. Pat. No. 3,215,265 to Welin-Berger discloses the use of a plurality of sheaths to protect patients from cross-contamination from thermometers. An inner package covers a thermometer, and may remain about the thermometer during insertion into a body orifice for temperature measurement. An outer package contains the inner package along with its contents.

U.S. Pat. No. 3,847,280 to Poncy discloses a sterile package for clinical thermometers and similar diagnostic equipment elements, where packaging may be stripped from sheathing surrounding the thermometer or other diagnostic equipment elements. Multiple layers and coatings are used, including ones for lubricants. One embodiment utilizes a plurality of packages that are attached in succession and separated by perforated sections for convenient separation.

U.S. Pat. Nos. 3,941,245 and 3,988,873 to Oliveriuis disclose the use of flexible, multi-layered containers, including a first container that slides within a second container, for containing and securing contaminated articles.

U.S. Pat. No. 4,057,731 to Loseff discloses a sterile container for X-ray cassette holders that also includes means for securing it to the body portion being X-rayed, i.e., straps and pressure-sensitive adhesives. In addition, a transparent wind is available, through which the internally located X-ray cassette maybe visualized. A flap/cuff may be used at the mouth of the container.

U.S. Pat. No. 4,445,241 to Ender. et al. discloses an air tight, multi-layered cover for pillows, mattresses and other padded objects. A complicated series of filters is disposed between compartments therein.

U.S. Pat. No. 4,770,911 to Sengewald discloses a cover for surrounding an operating table surface. Basically, a hose is closed at one end, and pulled over a cantilevered table surface, for example.

U.S. Pat. No. 4,902,453 to Ernst discloses a disposable envelope for enclosing an X-ray cassette designed to retard or prevent the spread of infections to or from the patient. Two sheets each of two layers (polyethylene inner layer; polyester outer layer) are heat sealed on three sides to form a pocket.

U.S. Pat. No. 4,923,453 to Bullard. Jr. discloses a disposable cover for use on X-ray and other similar tables used in medical settings. A three-layer construction is used, the middle layer of which is a fluid absorbent layer.

U.S. Pat. No. 5,050,256 to Woodcock discloses a bedding cover system designed for use in situations in which allergies to mites are problematic. Materials are used that are permeable to water but constitute barriers to mites, for example, by using pores generally less than 10 microns. Applications include use as mattress covers and as pillow covers.

U.S. Pat. No. 5,123,535 to Patnode, et al. discloses a flexible sterile bag for covering an X-ray cassette. Pressure-sensitive adhesive coatings on opposing end cuff portions permit ready closure of the bag by pressing the two cuffs together.

U.S. Pat. No. 5,228,851 to Burton discloses a protective sleeve that is designed to be placed on the handle of a medical or dental instrument to prevent the transmission of bacteria, etc., from one patient to another.

U.S. Pat. No. 5,343,861 to Herman discloses a disposable tonometer cover and packaging method designed to prevent infection in tonometry eye testing. A receptacle in the general shape of the applanation tip is used to directly contact the eye to determine the internal pressure thereof, and a peal-away cover is also incorporated.

U.S. Pat. No. 5,365,023 to Lawton discloses an elastic latex, disk-shaped cover for fitting over various stethoscope heads.

U.S. Pat. No. 5,446,897 to Ross. et al. discloses a dispenser apparatus for dispensing disposable stethoscope diaphragms. The apparatus is designed to prevent the spread of infections.

U.S. Pat. No. 5,541,972 to Anthony discloses a padded, sterile covering that fits over the face and about the edges of an X-ray plate that is used for mammography.

U.S. Pat. No. 5,554,098 to Yabe, et al. discloses a disposable protection cover for the tip of an endoscope, as well as a separate cover for other sections of the endoscope.

U.S. Pat. No. 5,564,431 to Seward discloses a flexible stethoscope cover and dispensing/packaging system for the head of a stethoscope. The cover basically is a rolled tube that is unrolled to cover a stethoscope head, much in the manner that a condom is applied.

U.S. Pat. No. 5,566,410 to Schaechter discloses a pillow cover that is designed for quick sealing by a hook-and-loop closure (Velcro™, for example). Other than the sealing means, the pillow cover is conventional.

U.S. Pat. No. 5,599,093 to Hoftman, et al. discloses a disposable combination light cover and handle for use with a conventional operating room light fixture to prevent the spread of infectious agents. The cover/handle basically consists of a closed-end tube that fits over a rod-like handle on a surgical light fixture, plus an annular flange/lip about the open end of the cover/handle.

In the realm of X-ray cassettes and similar medical and dental devices that come in direct contact with healthcare workers and patients, as well as in the realm of items common to the household and to the hospitality industry, a need exists for disposable covers that include a simple constellation of features not all available in any one or any combination of the above-cited disclosures. The covers must be simple in construction (ideally including only a single layer, but possibly including two or more layers), and capable of easy and inexpensive production. The covers must be disposable. The covers must be transparent to X-rays if the object being covered is an X-ray cassette or other X-ray recording device. The covers must not permit the passage of bacteria and other disease causing organisms (pathogens) to pass from one side to the other. For example, organisms on an X-ray cassette must not be able to come in contact with a patient or healthcare worker, and, likewise, organisms on or in a patient or healthcare worker must not be able to penetrate the covers and thereby contaminate the X-ray cassettes or other medical devices protected by the covers. With respect to bedding and other applications (e.g., covers for equipment, faucet handles and other handles, etc.), the covers similarly must not permit the passage of pathogens from one side of the covers to the other. The covers must also be non-reactive with typical human skin so as not to produce irritation or contact dermatitis. The covers must be capable of easy and quick application for covering the desired object. Finally, the covers must be easily sealable or attachable, where applicable; and, where the application requires adhesive contact with human skin, the adhesive must not irritate the skin, or produce a contact dermatitis.

SUMMARY OF THE INVENTION

The series of embodiments of the present invention achieve a variety of results and applications. Thus, it is an object of the present invention to provide a disposable, sealable bag or envelope structure for encasing an X-ray cassette or other X-ray recording device, surgical instrument, or diagnostic instrument, bedding, table or chair seat surface, faucet handle or other handle, etc., in a way that prevents the spread of bacteria and other pathogens among multiple persons using the same object.

It is another object of the present invention to provide multiple, optional, closure/sealing methods for a disposable bag or envelope structure for encasing an X-ray cassette or other X-ray recording device, surgical instrument or diagnostic instrument, bedding, table or chair seat surface, faucet handle or other handle, etc., including but not limited to adhesive (including, for example, adhesive strips that are covered with a protective sheet when not in use), heat sealing, hook-and-loop structures (for example, Velcro™), Ziplock™, and tucked flaps.

It is another object of the present invention to provide a disposable, sealable bag for encasing an X-ray cassette or other X-ray recording device, surgical instrument or diagnostic equipment, bedding, table or chair seat surface, faucet handle or other handle, etc., where the opening of the bag incorporates a slit at one or more edges to facilitate entry and positioning of the object therein.

It is yet another object of the present invention to provide a disposable flat sheet for covering the front of an X-ray cassette or other X-ray recording device, surgical instrument or diagnostic instrument, bedding, table or chair seat surface, toilet seat, faucet handle or other handle, etc., by merely folding ends over to attach by adhesive to the back of an object.

It is yet another object of the present invention to provide a disposable bag structure for covering an X-ray cassette or other X-ray recording device, surgical instrument or diagnostic instrument, table or chair seat surface, faucet handle or other handle, bedding, etc., where the disposable bag structure is part of a continuous structure of end-to-end bags that may be stored in rolled form, and with perforations or other scoring between adjacent bags to facilitate their separation when ready for use.

It is yet another object of the present invention to provide a disposable, sealable bag that (prior to use) is folded back upon itself such that, when in use, the previously internal, sterile, folded-over bag surfaces become the external surfaces against which the skin of the patient or other person comes in contact. Such back-folded bags are intended for a broad range of applications, such as for X-ray cassettes, thermometers, pillows, mattresses, and surgical, diagnostic and other instruments, table or chair seat surface, faucet handle or other handle, etc.

It is yet another object of the present invention to provide a disposable bag for covering the front of an X-ray cassette or other X-ray recording device, or other surgical or diagnostic instrument by providing "end pockets" at each end of a flat sheet. Thus, the front surface of the object is covered, as well as the back surface at each end to the extent of the depth of the two "end pockets."

The present invention overcomes limitations in the prior art by providing a series of embodiments for covers for X-ray cassettes-or other X-ray recording devices, surgical or diagnostic or other instruments, bedding, faucet handles or other handles, table or chair seat surface, toilet seats, etc., that will prevent or at least greatly minimize the transmission and cross-infection of bacteria and other pathogens from patient to patient, from patient to healthcare worker, from healthcare worker to patient, etc. The covers may be made of any disposable material that is transparent to X-rays and also impervious to bacteria and other pathogens, such as non-woven cellulosic derivatives, including any of the huge array of plastics suitable for use against human skin, such as polyvinyl chloride (including homopolymers and copolymers thereof), polyesters, polyolefins, and other polymers.

In one embodiment, a flat bag is provided with an open end (optionally including one or more slits to facilitate the introduction and positioning of an object therein) and a closure means thereof. Another embodiment features a flat sheet with a pocket at each end. Yet another embodiment simply is a sheet with adhesive on one surface at each end, such that the object to be covered (for example, an X-ray cassette, table or chair seat surface, etc.) is placed face down on the sheet (or vice versa) and the two ends are folded back to stick to the back side of the object. Another embodiment uses a bag folded back upon itself (prior to use) such that, once the object to be covered is inserted into the bag (and thereby is partially covered to the depth of that portion of the bag), the folded-over section is pulled over the remaining portion of the object, and closure is effected. This latter embodiment thereby provides the advantage of a potentially totally clean and initially sterile outer covering.

The closure means may be adhesive, as mentioned above, or, where one portion or flap of the back meets another for closure, heat sealing, Ziplock™, folded flap, zipper, or hook-and-loop structures (such as Velcro™) may be utilized. In addition, "protected" adhesive closure means may be used where the adhesive area is covered with a removable strip until ready for closure.

Though the covers of the present invention are directed mainly to various medical, surgical and diagnostic apparatuses, they also apply to such areas as pillows and mattresses, faucet handles and other handles, table and chair seat surfaces, toilet seats, etc. Thus, by using the back-folded bag embodiment of the present invention, a pillow cover, for example, may be made that permits a patient to experience a totally clean surface on which to place his head or other body part.

BRIEF DESCRIPTION OF THE DRAWINGS

FIG. 3 is a perspective view of an embodiment with an "end pocket" at each end of a sheet that covers the front surface of an object.

FIG. 4 is a cross sectional view along line 4—4 of FIG. 3.

FIG. 5 is a perspective view of an embodiment in which a sheet of cover material and adhesive attachment means are used to cover just the front and back surfaces of an object.

FIG. 8 presents a perspective view of an empty bag whose internal surfaces are sterile.

FIG. 9 shows a cross sectional view of the internally sterile bag of FIG. 8 folded back upon itself as an object is positioned therein by pressing against one end of the bag.

FIG. 10 presents the cross sectional view of FIG. 9 with an open end of the bag being advanced in a direction to unfold the bag, and to cover the uncovered end of the object positioned therein.

DESCRIPTION OF THE PREFERRED EMBODIMENTS

In the following detailed descriptions, a flat object to be covered will be designated generally as A, and the cover therefor will be designated generally as B. In general, however, object A need not be flat. One use of the present invention is to provide an anti-fomitic cover for an X-ray cassette, which is but one object that can qualify as A. In other embodiments, A can be virtually any other medical, surgical or diagnostic equipment item or part thereof, particularly an item or part that may come into contact with human skin or clothing. In addition, A may represent any object that may be covered and that may come into contact with human skin or clothing, such as a pillow, a mattress or table or chair seat cover, a toilet seat cover, a faucet handle or other handle, etc., or A may be a body part (for example, a part covered by a diaper).

The cover B may be made of any disposable material that is transparent to X-rays (where applicable), that is suitable for contact with human skin (i.e., it does not cause irritation to the skin or contact dermatitis), and that also is impervious at least to bacteria and other pathogens of a similar size; furthermore, smaller pathogens (for example, viruses) ideally also will not penetrate the disposable material.

A variety of closure means may be employed for the embodiments of the present invention, including adhesives (for example, pressure-sensitive adhesives and adhesives "protected" by a strip when not engaged in closure), heat sealing, zipper, Ziplock™, tucked flap, and hook-and-loop means (for example, Velcro™).

Figure 1:
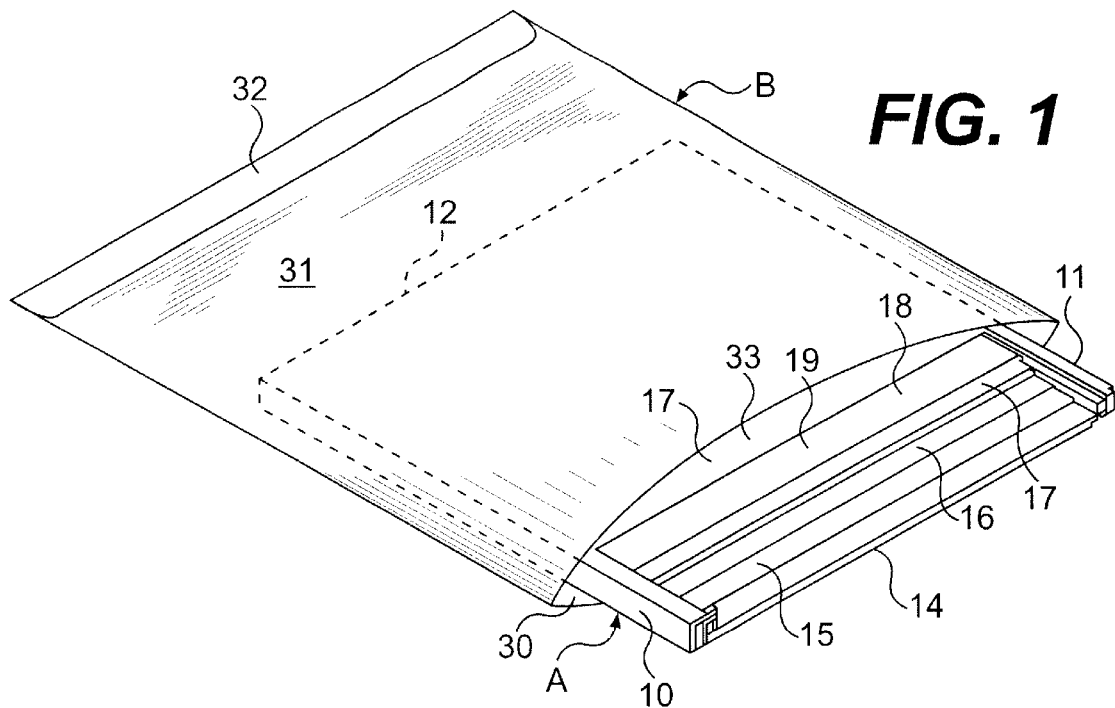
FIG. 1 represents a partially cut-away perspective view of a bag embodiment of the present invention for covering an object.
Figure 2:
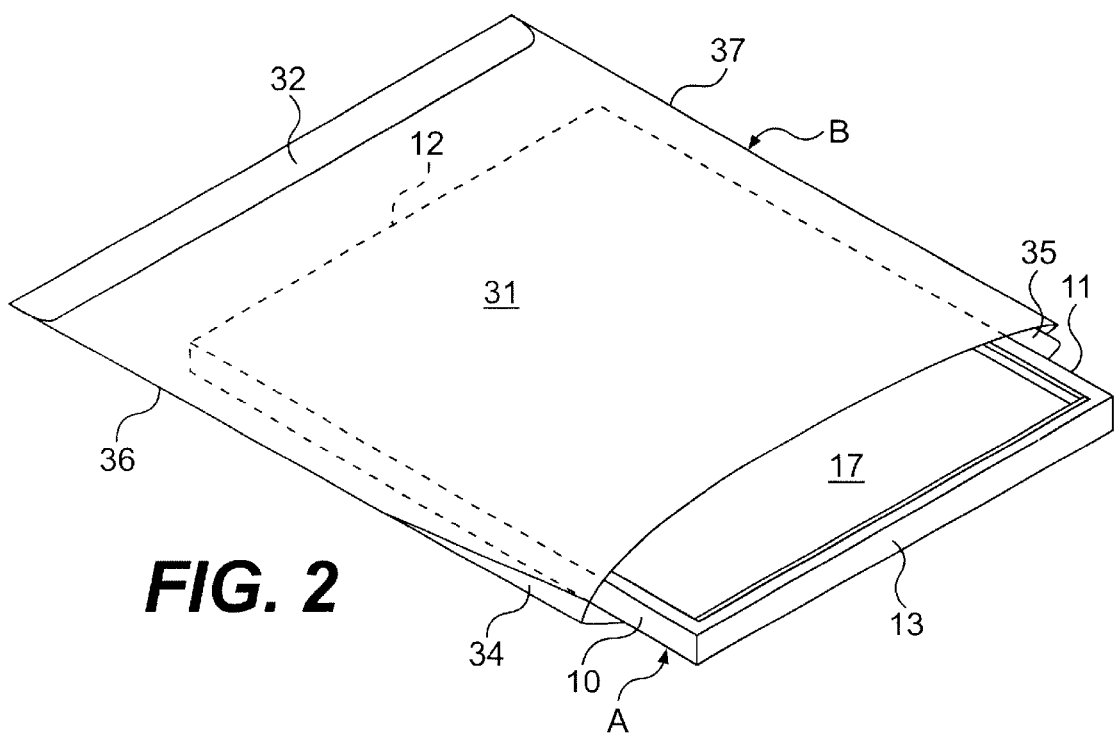
FIG. 2 represents a modification of the embodiment of FIG. 1, whereby slits are used at the closure end of the bag.

Referring to FIG. 1, A is featured as an X-ray cassette with sides (collectively forming a cassette frame) 10 and 11, and ends 12 and 13 (end 13 is cut away in FIG. 1 to show some of the structural elements of a typical cassette; see FIG. 2 for end 13 without a cut away). The X-ray cassette includes a front surface 14 that normally could contact the patient's skin in the area being X-rayed, intensifier screen 16, a sheet of X-ray film 15, and a back 17.

The cover A of FIG. 1 has the form of a bag or envelope with front 30, back 31, sealed end edge 32, and opening 33. Cassette B is inserted into opening 33 until it is completely covered. Any of the above listed closure means may be used to seal opening 33.

Referring to FIG. 2, X-ray cassette A is shown partially inserted into a bag similar to that in FIG. 1 with the exception of slits 34 and 35 at the opening. The slits may extend about ⅓ to ½ of the way down edges 36 and 37 of the bag. The purpose of slits 34 and 35 is to facilitate insertion of the cassette into the bag.

Referring to FIGS. 3 and 4, cover B is shown to comprise end pockets 38 and 39 and an intermediate portion 40 that covers the front surface 14 of the cassette. This embodiment is used by inserting cassette end 13 into end pocket 39, and cassette end 12 into end pocket 38. FIG. 4 represents the cross sectional view along line 4—4 of FIG. 3.

Referring to FIG. 5, cover B is shown as a single sheet 41 having ends 50 and 51. The inside of end 50 is provided with a coating of pressure-sensitive adhesive 42. The outside of end 51 is also provided with pressure-sensitive adhesive 43. The length of sheet 41 is sufficient to permit mutual contact of the entire widths of adhesive strips 42 and 43 when the sheet is wrapped around the cassette or other object to be covered. Any of the other closure means enumerated above may also be used.

Figure 6:
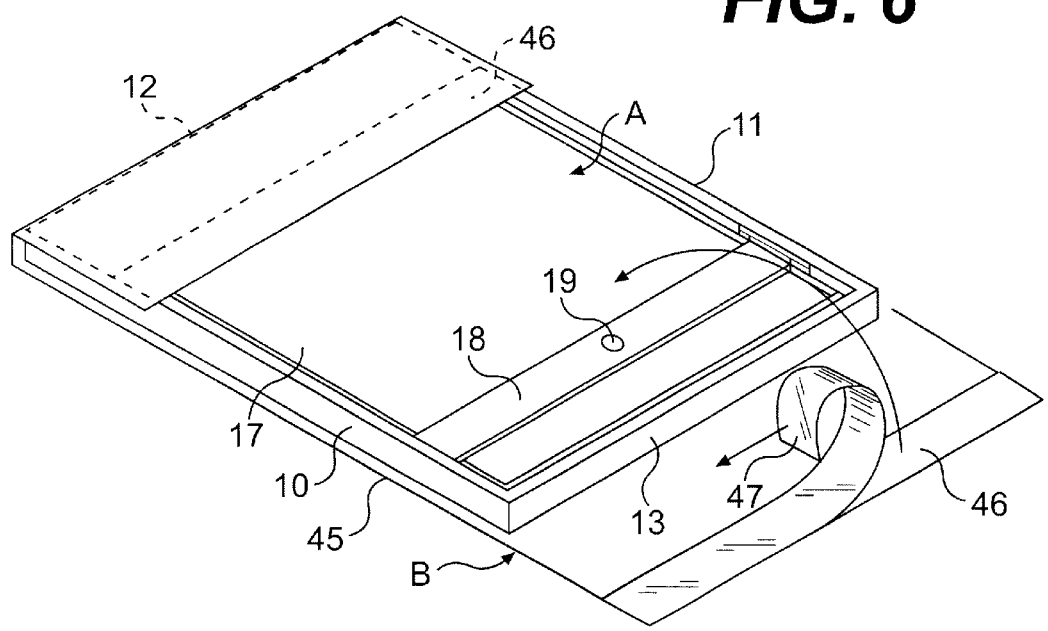
FIG. 6 presents a variation on the FIG. 5 embodiment in which the front of the object and the ends of the back are covered, with adhesive contacts being effected by the cover ends directly onto the back of the object.

Referring to FIG. 6, cover B is shown as a single sheet 45 that is coated with pressure-sensitive adhesive 46 at both ends, including a protective strip 47 that is removed by peeling just prior to application. In use, cassette A is positioned face down on the cover, protective strips 47 are removed, and the ends are wrapped around to the back, where the pressure-sensitive adhesive strips 46 engage the back 17 and optionally also sides 10 and 11 of the cassette.

Figure 7:
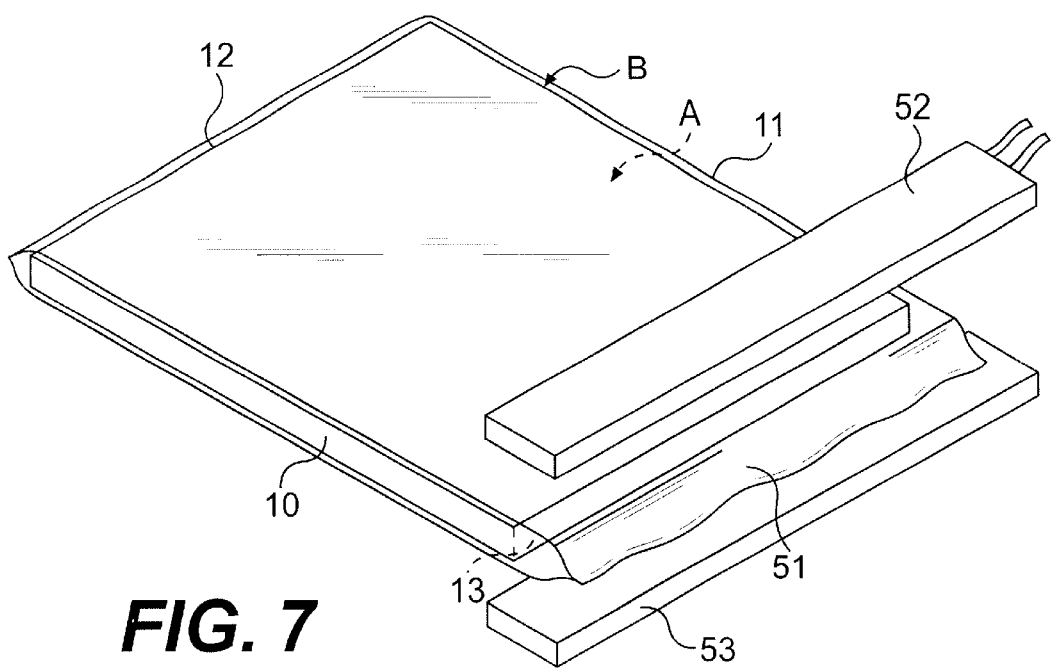
FIG. 7 is a perspective view showing sealing by means of heat sealing.

Referring to FIG. 7, heat sealable plastic cover/bag B (51) encloses cassette A, and end 51 is closed is by conventional heat sealing, for example with an impulse sealer or an electrically heated anvil 52, combined with companion anvil 53. In addition, with suitable plastic, the cover can be heat shrunk about the cassette by subjecting the cover to a short blast of hot air.

FIGS. 8, 9 and 10 are related, and show how a cover surface that will contact a patient can be kept sterile until shortly before use. Referring to FIG. 8, a plastic bag B has ends 55 and 56, a front 59, and a rear 60. Either or both ends 55 and 56 are sealed in such a manner that, while air-tight, they can be readily opened. This can be achieved by tack sealing or incorporation of a tear strip for the opening of a conventional heat seal. The remaining edges are sealed in any conventional air-tight permanent manner. The bag is prepared under sterile conditions such that at least the interior is sterile at time of use. In addition, end-to-end such bags may be prepared and stored on rolls, with appropriate scoring or perforations between the bags.

Referring to FIGS. 8 and 9, cassette A is pressed against one end of bag B, for example end 56, and forced in such a manner that the bag doubles back on itself to the point that end 56 abuts against end 55, and edge 12 of the cassette is flush against end 56. This operation may be aided by a sleeve-like jig (not shown) that fits around the cassette. Thereafter, sealed end 55 is opened fully, and the bag is peeled back on itself, as is shown in FIG. 10. Thus, the previously sterile inside surfaces of the bag are now on the outside of the bag, ready for engagement with the skin of a patient and free of bacteria and pathogens that may lurk on the surfaces of the cassette.

The inside-out principle demonstrated in FIGS. 8–10 may be applied to other objects, such as pillows, mattresses, table surfaces, thermometers, handles, parts of equipment, surgical equipment, etc.

One benefit of the inside-out principle of FIGS. 8–10 is that bacteria and other pathogens on the skin of a patient (for example, on hands holding the X-ray cassette in place, or on the skin of the body part being X-rayed) may thereby be eliminated from the cross-contamination cycle that otherwise would prevail in the clinical setting using conventional cassettes.

The above embodiments have emphasized use with X-ray cassettes, and in one embodiment use with pillows, mattress covers, table covers, etc. It is to be understood that the general concepts may be applied to a broad range of surgical or diagnostic equipment, as well as applications not specifically enumerated herein. Thus, it is intended that the specific embodiments presented herein are not limiting as to scope, but, rather, detail specific embodiments that may be generalized to a larger constellation of potential applications. The apparatus of the present invention is defined by the following claims.

I claim:

1. An anti-fomitic device for covering an object, comprising:
   a bag having a sterile interior and an exterior, the bag comprising:
      a material that is impervious to pathogens;
      a closed end; and
      a removably sealed open end,
   wherein, said bag is initially air-tight and when the removably sealed open end is opened, the bag is turned inside out to cover said object, resulting in the sterile interior being on the outside.

2. The anti-fomitic device according to claim 1, where the pathogen impervious material is a plastic selected from the group consisting of polyvinyl chloride, homopolymers of polyvinyl chloride, copolymers of polyvinyl chloride, polyesters, polyothylenes, polypropylenes, and polyolefins.

3. The anti-fomitic device according to claim 1, where the removably sealed open end further comprises a closure means.

4. The anti-fomitic device according to claim 3, where the closure is a means selected from the group consisting of heat sealing, pressure-sensitive adhesive, zipper, tucked flap, and hook-and-loop.

5. The anti-fomitic device according to claim 4, where the pressure-sensitive adhesive is protected with a strip of a material until the pressure-sensitive adhesive is needed.

6. The anti-fomitic device according to claim 5, where the strip is a material selected from the group consisting of paper and plastic.

7. The anti-fomitic device according to claim 1, further comprising said bag being dimensioned so as to enable covering of said object where the object is a member selected from the group consisting of X-ray cassettes, surgical devices, surgical instruments, diagnostic equipment, pillows, mattresses, faucet handles, toilet seats, table tops, and chair seats.

8. The anti-fomitic device according to claim 1, further comprising said bag and said removably sealed open end of said bag being dimensioned so as to enable covering of said object when said object comprises bedding.

9. The anti-fomitic device according to claim 8, wherein said bedding is selected from the group consisting of pillows and mattresses.

10. The anti-fomitic device according to claim 1, further comprising said bag and said removably sealed open end of said bag being dimensioned so as to cover a pillow.

11. The anti-fomitic device according to claim 1, further comprising said bag and said removably sealed open end of said bag being dimensioned so as to cover a mattress.

12. An anti-fomitic bag, consisting of:
   a closed bag which is initially air-tight and impervious to pathogens, said bag consisting of:
      an exterior;
      a sterile interior;
      an opening; and
      a sealed resealable closure for said opening, wherein the resealable closure is initially air-tight and adapted to be resealed after the resealable closure is opened and the bag inverted.

13. A method of providing an anti-fomitic cover to a separate object, comprising:
   providing a closed bag which is initially air-tight and impervious to pathogens, said bag including an exterior, a sterile interior, an opening and a sealed resealable closure for said opening;
   opening said resealable closure;
   inverting said bag over said separate object to have the sterile interior become a sterile outer surface; and
   resealing said closure to form said anti-fomitic cover.

14. The method of providing an anti-fomitic cover to an object of claim 13, wherein said object is chosen from the group consisting of pillows, mattresses, x-ray casettes, surgical and diagnostic equipment, toilet seats, table surfaces, seating surfaces, and clothing.

\* \* \* \* \*